United States Patent [19]
Pate

[11] Patent Number: 5,353,651
[45] Date of Patent: Oct. 11, 1994

[54] METHOD AND APPARATUS FOR SAMPLING WATER QUALITY IN A MUNICIPAL WATER SYSTEM

[76] Inventor: W. Richard Pate, 3508-B Sherry La., Tallahassee, Fla. 32303

[21] Appl. No.: 890,698

[22] Filed: May 29, 1992

[51] Int. Cl.⁵ .............................................. G01N 1/10
[52] U.S. Cl. ........................ 73/863.81; 73/861.85
[58] Field of Search .......... 73/863.81, 863.82, 863.85, 73/863.86

[56] References Cited

U.S. PATENT DOCUMENTS

| | | | |
|---|---|---|---|
| 2,576,893 | 11/1951 | Stewart, Jr. | 73/863.81 |
| 2,588,876 | 3/1952 | Quist | 73/863.81 |
| 2,926,527 | 1/1960 | Crandall | 73/863.81 |
| 2,986,939 | 6/1992 | Gould | 73/422 |
| 3,162,049 | 12/1964 | Blanchard | 73/863.85 |
| 3,625,251 | 12/1971 | Nelson | 137/614.04 |
| 4,056,981 | 11/1977 | Kalka et al. | 73/863.85 |
| 4,096,754 | 6/1978 | Beveridge, Jr. et al. | 73/432 R |
| 4,221,235 | 9/1980 | Maldavs | 137/614.04 |
| 4,294,124 | 10/1981 | Kalwaitis | 73/863.85 |
| 4,485,845 | 12/1984 | Brady | 137/614.04 |
| 4,524,811 | 6/1985 | Taylor | 73/863.81 |
| 4,925,627 | 5/1990 | Johnson | 73/863.82 |
| 4,998,954 | 3/1991 | Burr | 73/863.86 |
| 5,134,879 | 8/1992 | Wong et al. | 73/863.85 |
| 5,169,602 | 12/1992 | Pang et al. | 73/863.81 |

*Primary Examiner*—Hezron E. Williams
*Assistant Examiner*—George M. Dombroske
*Attorney, Agent, or Firm*—Allen, Dyer, Doppelt, Franjola & Milbrath

[57] ABSTRACT

A water sampling station installed adjacent the user of a residential water supply includes a housing, a cover removably fitted to the housing, a quick connect-disconnect coupler within the housing and a back flow preventer between the municipal water supply and the coupler. An elongated probe is provided with first and second ends and a quick connect-disconnect key at the first end and dimensioned for mating with the coupler of the sampling station, and with a shut off valve and back flow preventing valve adjacent the first end to prevent contamination at each sampling station. The sampling station may be installed in a residential user's meter box.

30 Claims, 4 Drawing Sheets

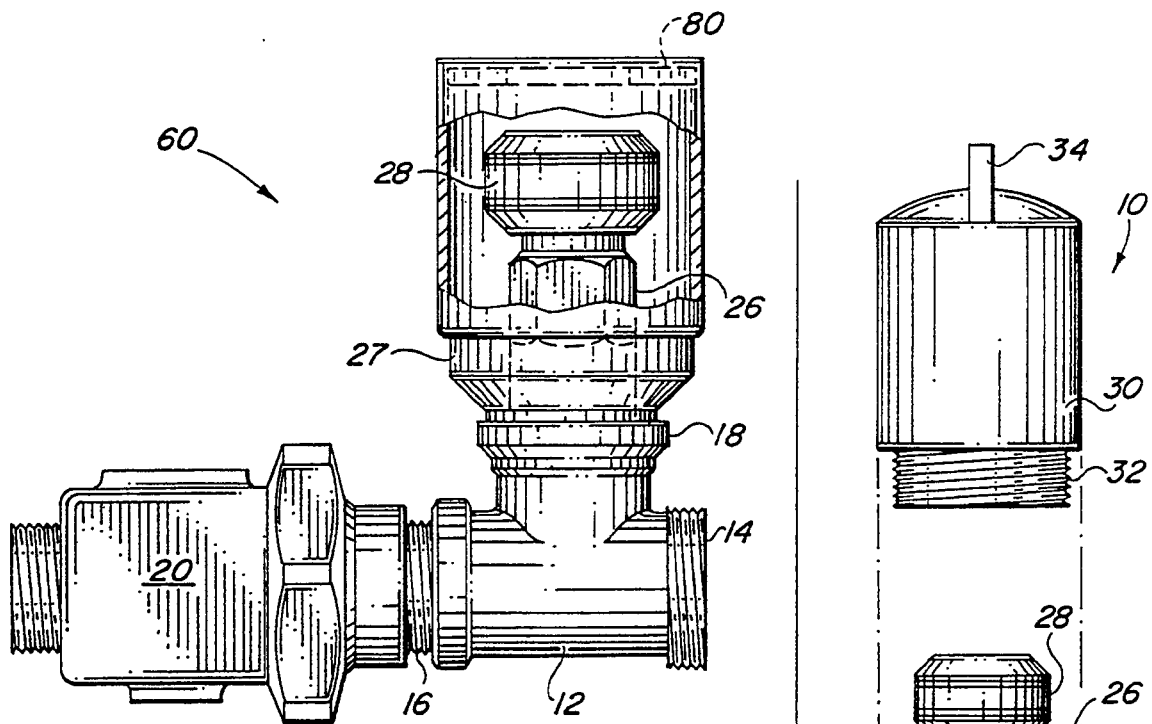
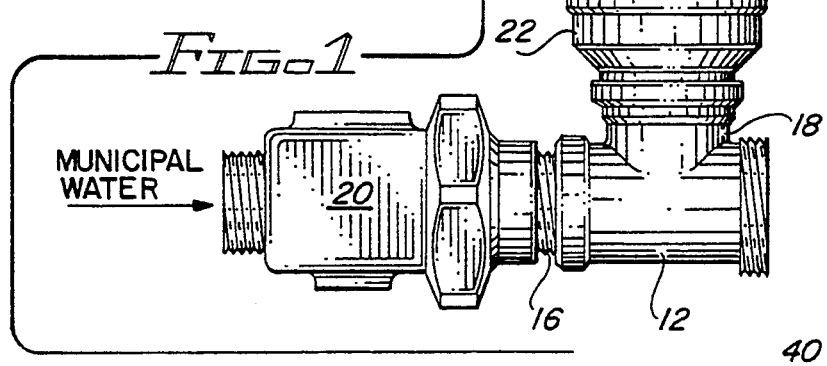
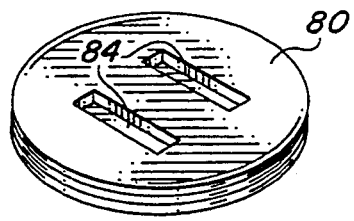
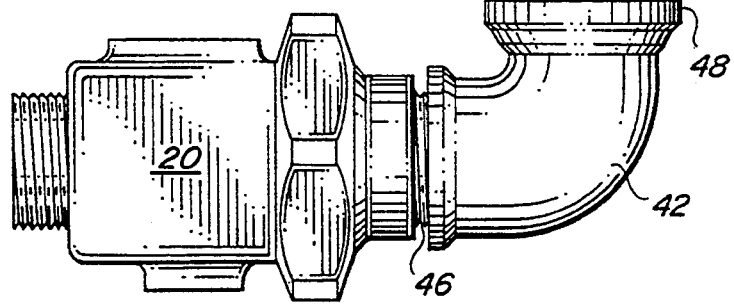

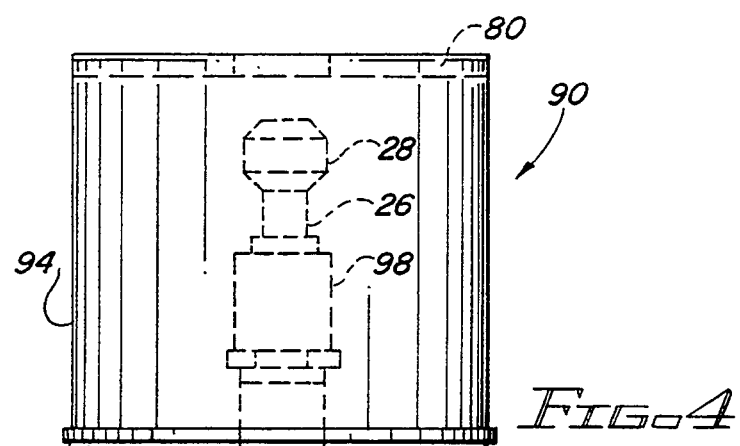
FIG.-4
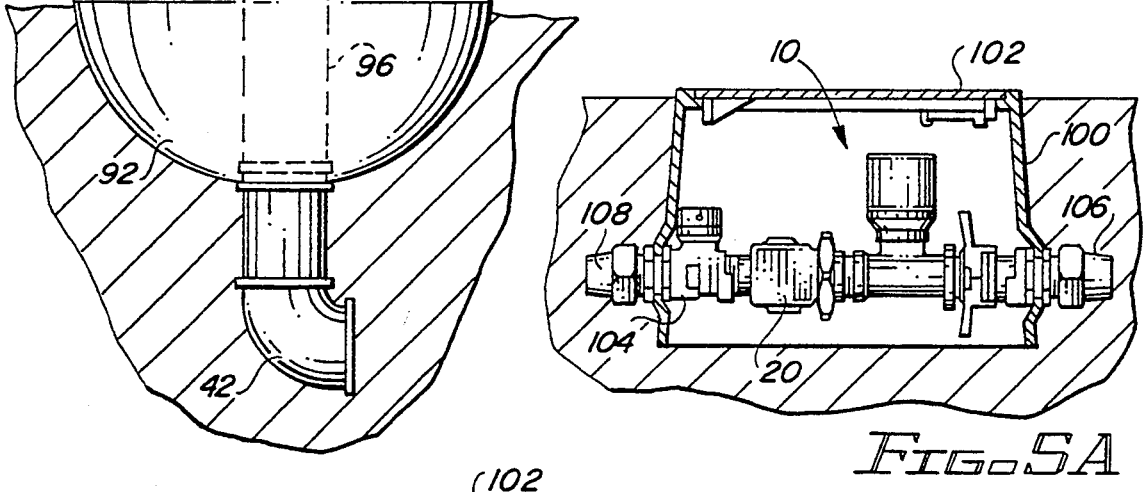
FIG.-5A
FIG.-5B
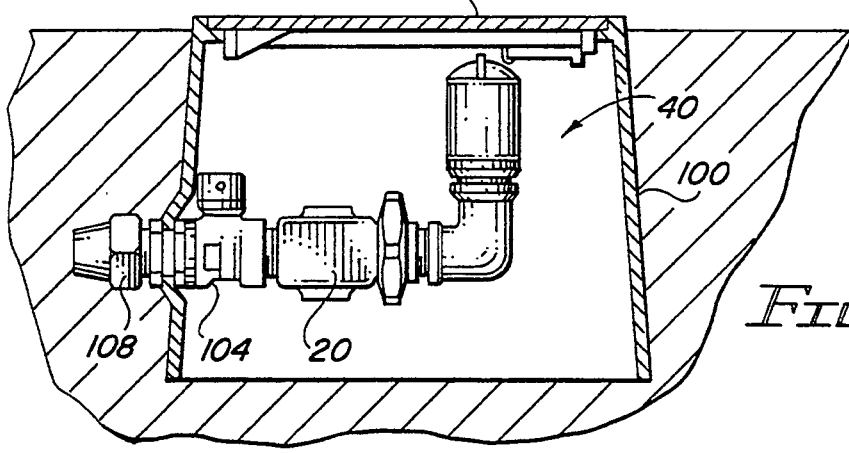
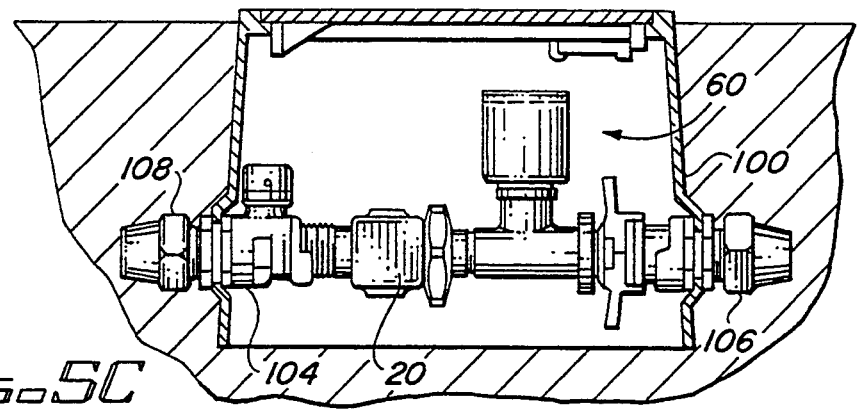
FIG.-5C

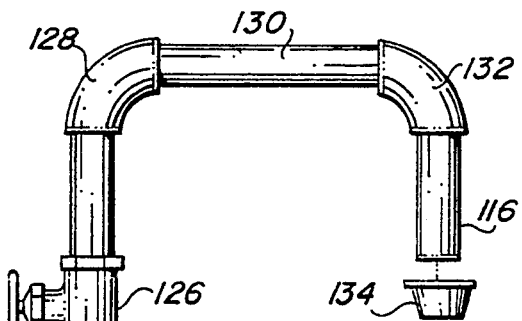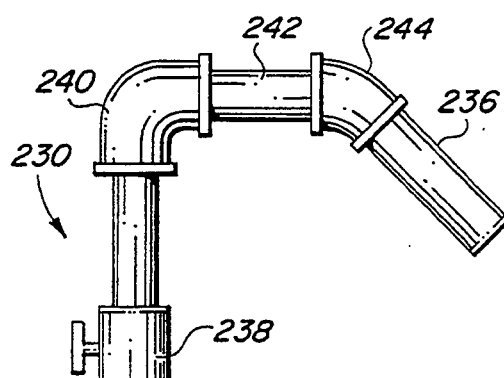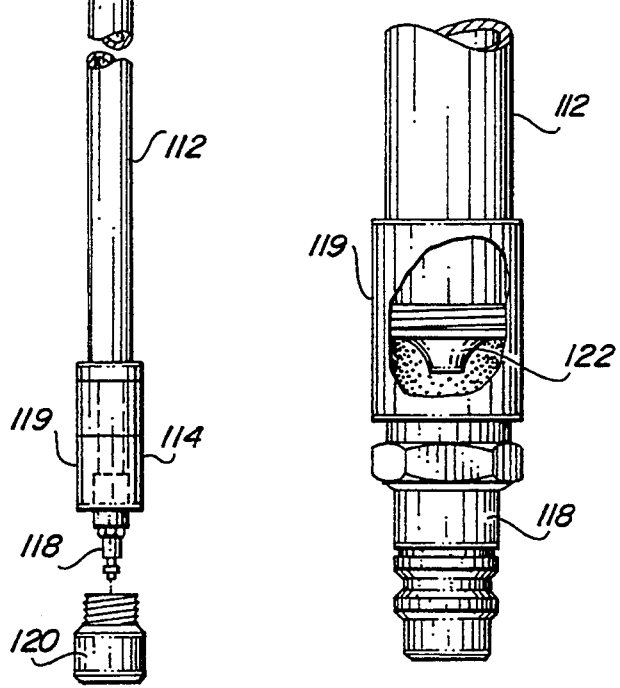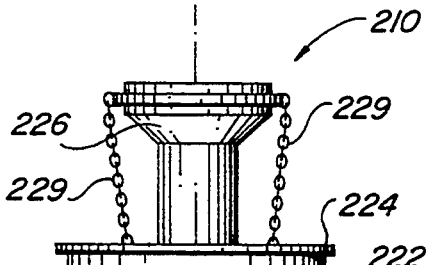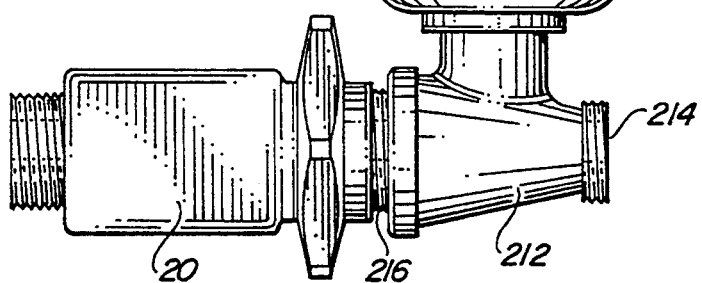

METHOD AND APPARATUS FOR SAMPLING WATER QUALITY IN A MUNICIPAL WATER SYSTEM

BACKGROUND OF THE INVENTION

The present invention is directed to methods and apparatus for drawing a sample of water from a municipal water system, in order to permit the testing of the quality of the water.

There are various techniques disclosed in the prior art for permitting the introduction of a removable probe into a pressurized fluid system, in order to draw off a sample of the fluid for testing purposes. See, for example, the arrangements disclosed by Beveridge et al in U.S. Pat. No. 4,096,754 and Gould in U.S. Pat. No. 2,986,939.

The prior art also discloses a variety of constructions for quick connect-disconnect couplers and valves, and examples of such arrangements are disclosed in the following U.S. Pat. Nos.: 4,221,235 to Maldavs; 4,485,845 to Brady; and 3,625,251 to Nelson.

SUMMARY OF THE INVENTION

The present invention has among its objectives the provision for apparatus and a related method for sampling water quality in a municipal waste water system. The apparatus includes a water sampling station having means dimensioned for coupling with a pipe in a municipal water system, the sampling station including a housing, a cover removably fitted to the housing, a quick connect-disconnect coupler within the housing and communicating with the coupling means and means for preventing cross-contamination between the municipal water supply and the coupler. An elongated probe rod is provided having first and second ends with a quick connect-disconnect key at the first end and which is dimensioned for mating with the coupler of the sampling station. The probe includes a back-flow preventing means adjacent the first end and a discharge opening at the second end.

In the preferred form of the sampling apparatus, the cross-contamination means comprises a dual check valve between the water sampling station and the municipal water supply. The water sampling station may be either located in the supply line between the source of municipal water and a user, or on a terminating elbow coupled to the water supply. The housing may be positioned below ground, for example within the confines of a residential meter box, or alternatively may be positioned with a portion of the housing extending above ground level.

Further in accordance with the present invention, the probe rod is preferably provided with a shut off valve between the first and second ends, and has at least one bend adjacent the second end so that water flows first upwardly and vertically through the rod and is then directed horizontally through the bend. The water may be then directed through a second bend so that the sample exits the second end in a generally vertical direction.

In one form, the quick connect-disconnect coupler comprises a spring loaded normally closed valve, with the probe rod having a sleeve at the first end for engaging the spring-loaded valve to thereby overcome the spring load and cause the opening of the valve.

In use, the operator accesses the water sampling station through the residential meter box and the cap covering the water sampling station, inserts the first end of the probe rod into the quick connect-disconnect coupler of the water sampling station to effectuate flow of water through the probe rod and out the second end, operates the shut off valve to prevent the further flow of water through the probe rod, and then withdraws the first end of the probe rod from the quick connect-disconnect coupler by a vertical movement of the entire probe rod upwardly. Cross-contamination of standing water in the probe rod is prevented with a check valve positioned at the first end of the probe rod. It will be appreciated that a plurality of the water sampling stations will be installed at various locations along a municipal water supply system, to permit the operator of the system to quickly and easily access the various water sampling stations to draw out samples for testing water quality. Because the water sampling station may be easily integrated into a customer's ground-level meter box, then the requirements for obtaining water samples may be realized with a minimum of both installation and operating expense.

THE DRAWING

FIG. 1 is a side view illustrating one form of a water sampling station in accordance with the present invention.

FIG. 2 is a side view of a second form of a water sampling station.

FIGS. 3A and 3B are side and perspective views, respectively, of a third form of a water sampling station.

FIG. 4 is a side view of a fourth form of a water sampling station in accordance with the present invention, in which a portion of the construction hidden from view is shown in dotted lines.

FIGS. 5A, 5B and 5C are side views illustrating the manner in which the water sampling stations of FIGS. 1, 2 and 3, respectively, are installed below ground level within the confines of a residential meter box.

FIG. 6A is a side elevation illustrating a probe rod useful with the water sampling stations of FIGS. 1–4, in accordance with the present invention.

FIG. 6B is a side view of a portion of the probe rod of FIG. 6A, partially broken away.

FIG. 7 is a side elevation illustrating another form of the quick connect-disconnect coupler used in the water sampling station.

Figure 8:
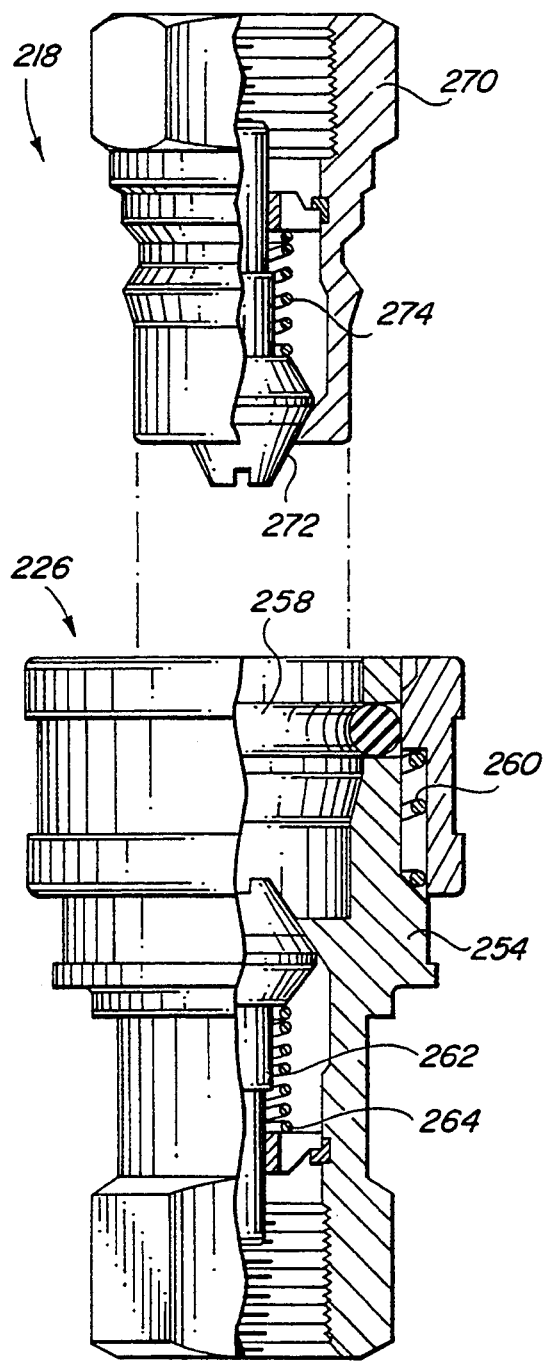
FIGS. 8 and 9 illustrate details of the quick connect-disconnect coupler shown in FIG. 7.

In all of the views, common reference numerals are used to designate the same feature or element.

DETAILED DESCRIPTION

A first form of a water sampling station according to this invention is referred to generally by the reference numeral 10 in FIG. 1. The sampling station 10 includes a "T" union 12 having threaded ends 14, 16 and a throat 18. The union 12 is coupled via thread 16 to a dual check back flow preventer, which in turn is coupled to a source of municipal water. Back flow preventers of this type are well known in the art, and are not described in detail here.

The throat 18 is threaded to receive a housing 22 having a gasket 24 and into which is inserted a quick connect-disconnect coupler 26 in the form of a valve having an upper ball 28 adapted to receive a sliding fit key which opens the valve 26 and permits the flow of water through the ball.

The sampling station 10 further includes a housing cap 30 having threads 32 adapted to engage the housing 22, and a gripping extension 34 for permitting removal of the cap 30.

A second form of the water sampling station is referred to generally by the reference numeral 40 in FIG. 2, and includes an elbow 42 having a threaded throat 48 adapted to receive the housing 22. Threads 46 of the elbow 42 are coupled to the back flow preventer 20. The construction of the sampling station 40 is otherwise the same as sampling station 10 in FIG. 1, and includes valve 26 and ball 28.

A third form of the water sampling station is shown in FIGS. 3A and 3B, and referred to there generally by the reference numeral 60. The sampling station 60 is essentially identical to the sampling station 10 of FIG. 1, except that the housing 72 extends upwardly a dimension greater than the ball 28, to completely enclose the valve 26 and ball 28. The upper extremity of the housing 72 is threaded to receive a covering plate 80 having two indentations 84 which are specifically dimensioned to receive a conventional meter wrench.

A fourth form of the water sampling station is shown in FIG. 4 and referred to generally by the reference numeral 90. The sampling station 90 includes the elbow 42 and a vertical extension pipe 96 which extends above ground level. The housing is formed of a bell-shaped base 92 extending substantially below ground level and an upper housing portion 94 extending above ground level and threaded to receive the cover 80. A station support 98 is fitted within the housing 94 and is dimensioned to receive the valve 26 and ball 28.

The manner in which the various forms of the water sampling station may be installed in a residential meter box is illustrated in FIGS. 5A, 5B and 5C. In FIG. 5A, a residential meter box 100 is shown installed below ground in a conventional manner with a cover 102. In accordance with the present invention, the water sampling station 10 of FIG. 1 is installed within the box 100, between the outlet 106 to the residential user and the inlet 108 from the municipal water supply, with the back flow preventer 20 and a curb valve 104 between the sampling station 10 and the inlet 108.

In the example of FIG. 5B, the second form of the water sampling station 40 is installed within the meter box 100, but of course is not coupled to the user's facility, but instead is coupled to the inlet 108 of the municipal water supply through the curb valve 104.

In the arrangement of FIG. 5C, the third form of the water sampling station 60 is contained within the residential meter box 100 below ground, and is coupled in the same manner as the sampling station 10 in FIG. 5A. In both FIGS. 5A and 5C, the box 100 has the same laying dimension between the inlet and the outlet.

Construction details of the probe rod are shown in FIGS. 6A and 6B. In FIG. 6A, the probe rod is referred to generally by the reference numeral 110 and includes a vertical tubular rod portion 112 extending between a first, input end 114 and a second, outlet end 116. The probe rod 110 includes at the first end 114 a protective housing 119 and cap 120, within which is positioned a valve key 118 which is dimensioned to operate the quick connect-disconnect coupler 26 of FIGS. 1–4, as well as the spring-loaded valve 226 described in greater detail below with reference to FIGS. 7–9. As shown in FIG. 6B, the probe rod tubing 112 includes a ball check valve 122 at the first end 114, to prevent water standing in the probe rod tubing 112 to return through the coupler 26 to the water sampling station.

The probe rod 110 further includes an O-ring seal 124 along its length, which in turn couples additional tubing through a shut off valve 126 to a first elbow 128, which directs the flow of water horizontally through tubing 130 to a second elbow 1322 and thence out of the second end 116 through a protective seal 134.

It will thus be appreciated by those skilled in the art that the combination of any of the water sampling stations shown in FIGS. 1–4 (and installed within the confines of a residential meter box as shown in FIGS. 5A–5C) combined with the probe rod 110 of FIGS. 6A and 6B provides an extremely useful apparatus and method for easily and quickly drawing samples of municipal water for purposes of testing water quality.

Another form of the quick connect-disconnect coupler useful with the various water sampling station constructions shown in the drawings and described above will now be described with reference to FIGS. 7–9.

In FIG. 7, water sampling station is referred to generally by the reference numeral 210 and includes a union 212 having opposing end threads 214, 216, the latter of which is coupled through a back flow preventer 220 to a source of municipal water. The T coupling 212 is threaded with a base of a housing 222, which has a corresponding cap (not shown) dimensioned to join with the housing 222 at gasket 224. A quick connect-disconnect valve 226 which is spring loaded into a normally closed position is provided, and includes a flexible retainer, such as chains 229, which retain the spring action of the valve 226, as described in greater detail below with reference to FIGS. 8 and 9.

The apparatus of FIG. 7 further includes a probe rod 230, which is similar to the probe rod 110 of FIGS. 6A and 6B, and includes a vertical probe rod pipe 232 communicating through a shut off valve 238, elbows 240 and 244, horizontal tubing 242 to an outlet end 236. The first end 234 of the probe rod 230 includes a key 218 which is dimensioned to extend into the valve 226, and then unlocking plate 219 which is adapted to overcome the spring load of the valve 226, to thereby permit the valve to be opened so that water communicates through the key 218 and out of the outlet end 236 of the probe rod 230.

Figure 9:
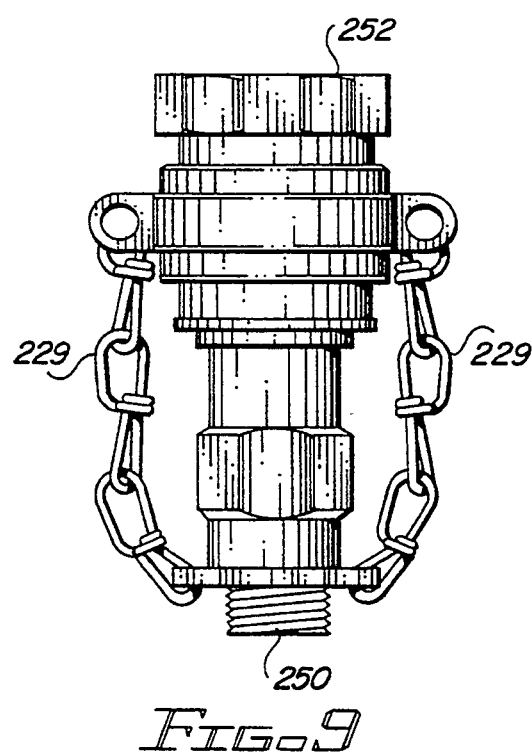

The details of the valve 226 and the valve key 218 are shown in FIGS. 8 and 9, where the valve 226 includes an outer sleeve 254 having an inner valve element 262 which is biased by spring 264. The sleeve 254 includes a throat 256 extending generally vertically and a sealing gasket 258. In turn, the probe rod key 218 includes a sleeve 270 dimensioned to extend into the throat 256 and tightly conform to gasket 258 to avoid leakage. The key 218 includes an extension 272 which is biased by spring 274. In use, the key 218 is extended into throat 256 of valve 226, with the extension 272 and the valve element 262 engaging each other and causing the unloading of their respective springs 264, 274. Because sleeve 260 is itself spring biased, extension member 272 is able to reach the valve element 262, as its associated spring 258 is overcome.

As shown in FIG. 9, the valve 226 includes a cover 252 and threads 250 for permitting a joinder to the union 212 (FIG. 7).

This concludes the description of the preferred embodiments. A reading by those skilled in the art will bring to mind various changes without departing from the spirit and scope of the invention. It is intended, however, that the invention only be limited by the following appended claims.

What is claimed is:

1. A system for sampling water quality in a municipal water system, comprising in combination:

at least one residential meter box; and a water sampling station having means dimensioned for coupling with a pipe in a municipal water system, the sampling station including a housing, a cover removably fitted to the housing, a quick connect-disconnect coupler within the housing and communicating with the coupling means, and means for preventing cross-contamination between the municipal water supply and the coupler;

an elongated probe rod having first and second ends with a quick connect-disconnect key at the first end and dimensioned for mating with the coupler of the sampling station, back-flow preventing means adjacent the first end, and a discharge opening at the second end;

means for dimensioning the water sampling station for an installation into the residential meter box; and wherein said water sampling station is installed in at least said one residential meter box.

2. The apparatus recited in claim 1 wherein the means for preventing cross-contamination comprises a dual check valve between the water sampling station and the municipal water supply.

3. The apparatus recited in claim 2 wherein the housing and cover are threaded together for rotational removal of the cover to permit access to the coupler, the cover having slots dimensioned to receive a conventional water meter wrench.

4. The apparatus recited in claim 2 wherein the station is located in a water supply line between the municipal water supply and a user.

5. The apparatus recited in claim 2 wherein the sampling station is located on a terminating elbow coupled to the municipal water supply.

6. The apparatus recited in claim 5 wherein the housing of the station extends above ground level and the terminating elbow is below ground level.

7. The apparatus recited in claim 1 wherein the probe rod has a shut-off valve between the ends thereof.

8. The apparatus recited in claim 7 wherein the probe rod extends through at least one bend adjacent the second end so that water flowing upwardly and vertically through the rod is directed horizontally.

9. The apparatus recited in claim 8 wherein the shut-off valve is along the probe rod between the bend and the first end.

10. The apparatus recited in claim 8 wherein the probe rod extends through a second bend between the one bend and the second end, so that water exits the second end in a generally vertical direction.

11. The apparatus recited in claim 1 further comprising means at the first end of the probe rod for engaging and actuating the quick connect-disconnect coupler.

12. The apparatus recited in claim 11 wherein the engaging and actuating means comprise an outer sleeve about the probe rod at the first end.

13. A system for sampling water quality in a municipal water system, comprising in combination:

at least one residential meter box; and a water sampling station having means dimensioned for coupling with a pipe in a municipal water system, the sampling station including a housing, a cover removably fitted over the housing, a normally closed, spring-loaded quick connect-disconnect valve within the housing and communicating with the coupling means, and means for preventing cross-contamination between the municipal water supply and the coupler;

an elongated probe rod having first and second ends and means at the first end for engaging and opening the spring loaded quick connect-disconnect valve, the probe rod further comprising back-flow preventing means along the probe and a discharge opening at the second end;

means for dimensioning the water sampling station for an installation into a residential meter box; and wherein said water sampling station is installed in at least said one residential meter box.

14. The apparatus recited in claim 13 wherein the means for preventing cross-contamination comprises a dual check valve between the water sampling station and the municipal water supply.

15. The apparatus recited in claim 14 wherein the housing and cover are threaded together for rotational removal of the cover to permit access to the coupler, the cover having slots dimensioned to receive a conventional water meter wrench.

16. The apparatus recited in claim 14 wherein the station is located in a water supply line between the municipal water supply and a user.

17. The apparatus recited in claim 14 wherein the sampling station is located on a terminating elbow coupled to the municipal water supply.

18. The apparatus recited in claim 17 wherein the housing of the station extends above ground level and the terminating elbow is below ground level.

19. The apparatus recited in claim 13 wherein the probe rod has a shut-off valve between the ends thereof.

20. The apparatus recited in claim 19 wherein the probe rod extends through at least one bend adjacent the second end so that water flowing upwardly and vertically through the rod is directed horizontally.

21. The apparatus recited in claim 20 wherein the shut-off valve is along the probe rod between the bend and the first end.

22. The apparatus recited in claim 20 wherein the probe rod extends through a second bend between the one bend and the second end, so that water exits the second end in a generally vertical direction.

23. The apparatus recited in claim 13 further comprising means at the probe rod first end for opening the valve by overcoming its spring load.

24. A method for sampling water quality in a municipal water system, comprising the steps of:

coupling a water sampling station with a source of municipal water and installing a quick connect-disconnect coupler in the station;

preventing cross-contamination between the municipal water source and the coupler;

drawing water through an elongated probe rod with a quick connect-disconnect key dimensioned for mating with the coupler of the sampling station at a first end thereof;

preventing back flow of water in the probe rod through the first end; and dimensioning the water sample station for, and then installing the water sampling station in, a residential meter box.

25. The method recited in claim 24 wherein the step of preventing cross-contamination between the municipal water supply and the coupler comprises the step of installing a dual check valve between the water sampling station and the municipal water supply.

26. The method recited in claim 24 further comprising the step of installing the sampling station between a municipal water supply line and a user.

27. The method recited in claim 25 further comprising the step of installing the water sampling station at a terminating elbow coupled to the municipal water supply.

28. The method recited in claim 27 further comprising the step of installing the sampling station with the housing extending above ground level and with a terminating elbow extending below ground level.

29. The method recited in claim 24 further comprising the step of fitting a shut-off valve along the probe rod between the ends thereof, and operating the shut-off valve after drawing out the water sample.

30. The method recited in claim 24 further comprising the step of installing a check valve adjacent the first end of the probe rod for preventing the back flow of standing water out of the probe rod and into the water sampling station.

* * * * *